US008859031B2

(12) United States Patent
Walsh

(10) Patent No.: US 8,859,031 B2
(45) Date of Patent: Oct. 14, 2014

(54) EFFICIENT PATH COATING ON LABCOAT IPMP COATING SYSTEM

(75) Inventor: Gareth Walsh, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 342 days.

(21) Appl. No.: 13/243,717

(22) Filed: Sep. 23, 2011

(65) Prior Publication Data

US 2012/0171353 A1 Jul. 5, 2012

Related U.S. Application Data

(60) Provisional application No. 61/428,133, filed on Dec. 29, 2010.

(51) Int. Cl.
*A61L 33/00* (2006.01)
*B05D 1/26* (2006.01)

(52) U.S. Cl.
CPC ........................................ *B05D 1/26* (2013.01)
USPC ............. 427/2.25; 427/8; 427/421.1; 427/58; 118/300

(58) Field of Classification Search
USPC ........................................................ 427/2.25
See application file for complete search history.

(56) References Cited

U.S. PATENT DOCUMENTS

| | | | | |
|---|---|---|---|---|
| 7,048,962 | B2 | 5/2006 | Shekalim et al. | |
| 2004/0018296 | A1 * | 1/2004 | Castro et al. ................ | 427/2.25 |

FOREIGN PATENT DOCUMENTS

| | | | |
|---|---|---|---|
| EP | 2127617 | A1 | 12/2009 |
| WO | 2009/129579 | A1 | 10/2009 |

* cited by examiner

*Primary Examiner* — Dah-Wei D Yuan
*Assistant Examiner* — Andrew Bowman
(74) *Attorney, Agent, or Firm* — Vidas, Arrett & Steinkraus, P.A.

(57) ABSTRACT

A method of coating a medical prosthesis includes identifying coating points on the surface of the medical prosthesis and determining a coating pathway along which an applicator travels while coating the medical prosthesis. In some embodiments, the coating pathway minimizes the rotational movement of the medical prosthesis during the coating process. In other embodiments, the coating pathway minimizes the amount of time needed for the coating process.

15 Claims, 18 Drawing Sheets

EFFICIENT PATH COATING ON LABCOAT IPMP COATING SYSTEM

CROSS-REFERENCE TO RELATED APPLICATIONS

This application claims priority to provisional application No. 61/428,133 filed Dec. 29, 2010, the entire content of which is incorporated by reference.

STATEMENT REGARDING FEDERALLY SPONSORED RESEARCH

Not Applicable

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

One method to coat a medical prosthesis is a strip coating mode. Strip coating is a raster type of coating that follows a predefined regular path that does not depend upon strut geometry. An example of a stent pattern with some of the plurality of strip coating pathways is shown in FIG. 1*a*. FIG. 1*b* is an exploded view of the portion of FIG. 1*a* bounded by the box (upper left corner). As shown in FIG. 1*a*, each coating pathway extends from one end of the medical prosthesis to the other end of the medical prosthesis and each coating point is bisected by one coating pathway. The coating applicator deposits a drop onto coating points that are bisected by the pathway being traveled. As can be seen from FIG. 1*a*, based on the stent geometry and the number of coating points, the number of strip coating pathways can be numerous. The medical prosthesis or the coating applicator rotates about the longitudinal axis of the medical prosthesis in incremental steps to go from one pathway to the next pathway until the coating applicator has traveled along each coating pathway.

Another method of determining a coating pathway is a vector approach. In this method, the coating applicator travels along the strut centerline from one coating point to another coating point. An example of a stent pattern with a vector approach coating pathway is shown in FIG. 2. As can be seen in FIG. 2, each coating point is bisected by the coating pathway. Because the coating pathway travels along the strut centerline from coating point to coating point, the maximum angle of deviation depends upon the stent geometry. For a stent pattern with circumferential bands of struts that are longitudinally separated and that are connected one to another by connectors, the coating pathway does not extend longitudinally from one end of the medical prosthesis to the other end.

Commonly owned U.S. Pat. No. 7,048,962, incorporated by reference in its entirety, discusses raster coating and vector coating.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

A method of coating a medical prosthesis includes identifying coating points on the surface of the medical prosthesis and determining a coating pathway along which an applicator travels while coating the medical prosthesis. In some embodiments, the coating pathway minimizes the rotational movement of the medical prosthesis during the coating process. In other embodiments, the coating pathway minimizes the amount of time needed for the coating process. In one embodiment, a pattern based algorithm is used to determine a coating pathway. In another embodiment, a band algorithm is used to determine a coating pathway.

In at least one embodiment, the invention is directed to Efficient Path Coating. Efficient path coating is a method of determining a coating pathway for a medical prosthesis where the coating points are located on elements that are substantially parallel to the longitudinal axis of the medical prosthesis. In at least one embodiment the efficient path coating method is a combination of raster coating and vector coating. In one embodiment, the efficient path coating method uses band and angular limits that are predetermined to identify sets of coating points that lie on coating pathways and then uses a vector path to design the coating pathways.

These and other embodiments which characterize the invention are pointed out with particularity in the claims annexed hereto and forming a part hereof However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1*a* shows a plurality of strip coating pathways determined by PRIOR ART raster type coating.

FIG. 1*b* is an enlargement of the boxed portion of FIG. 1*a*.

Figure 13:
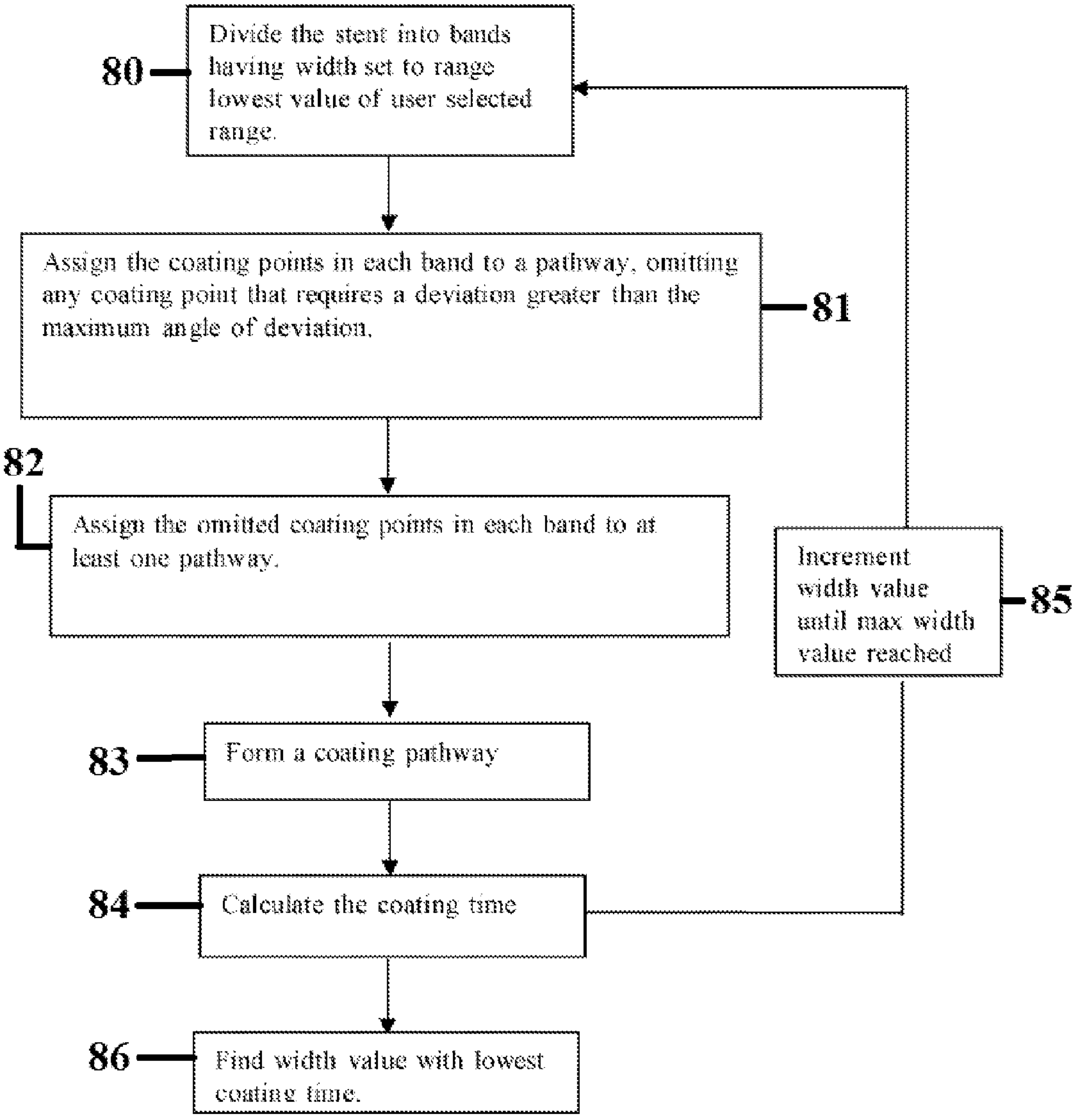
FIG. 13 is a flowchart of an algorithm to determine coating pathways.
Figure 15:
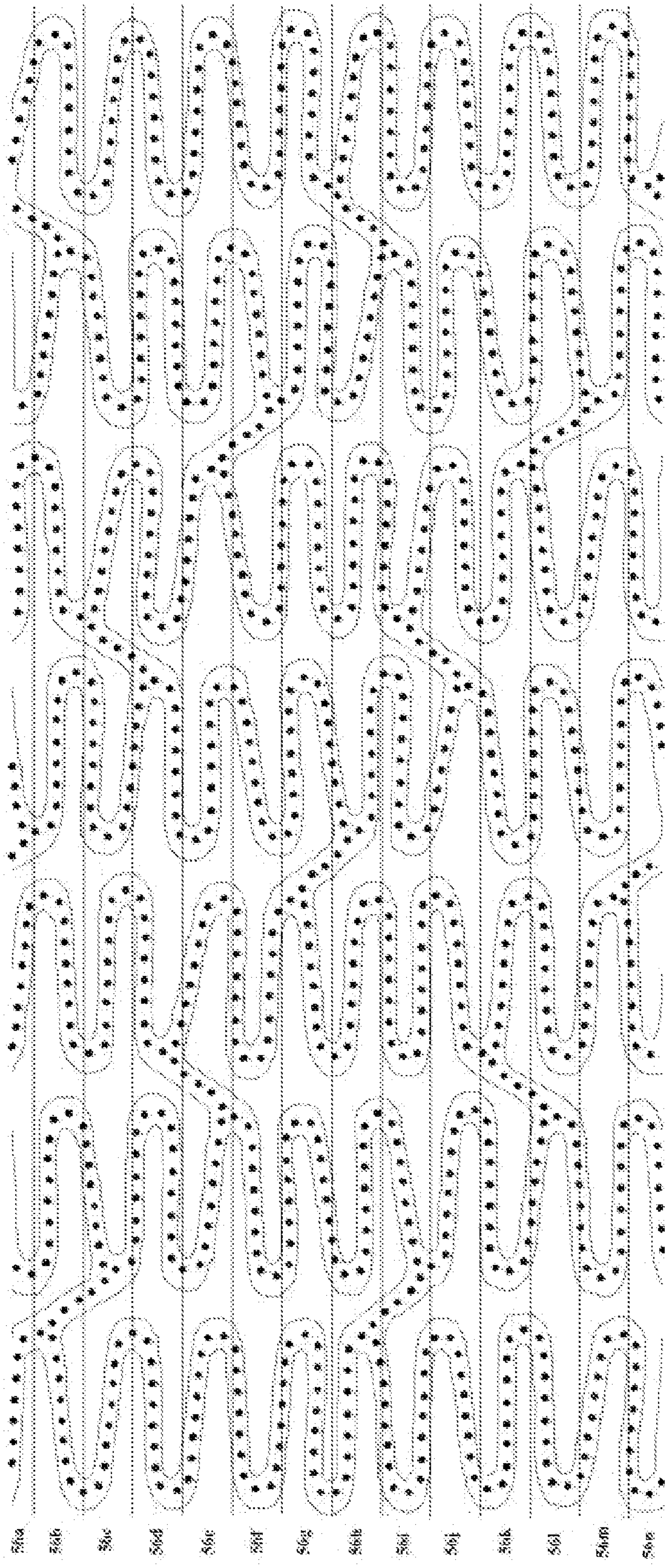
FIG. 15 is stent with coating locations divided into a plurality of bands.
Figure 16A:
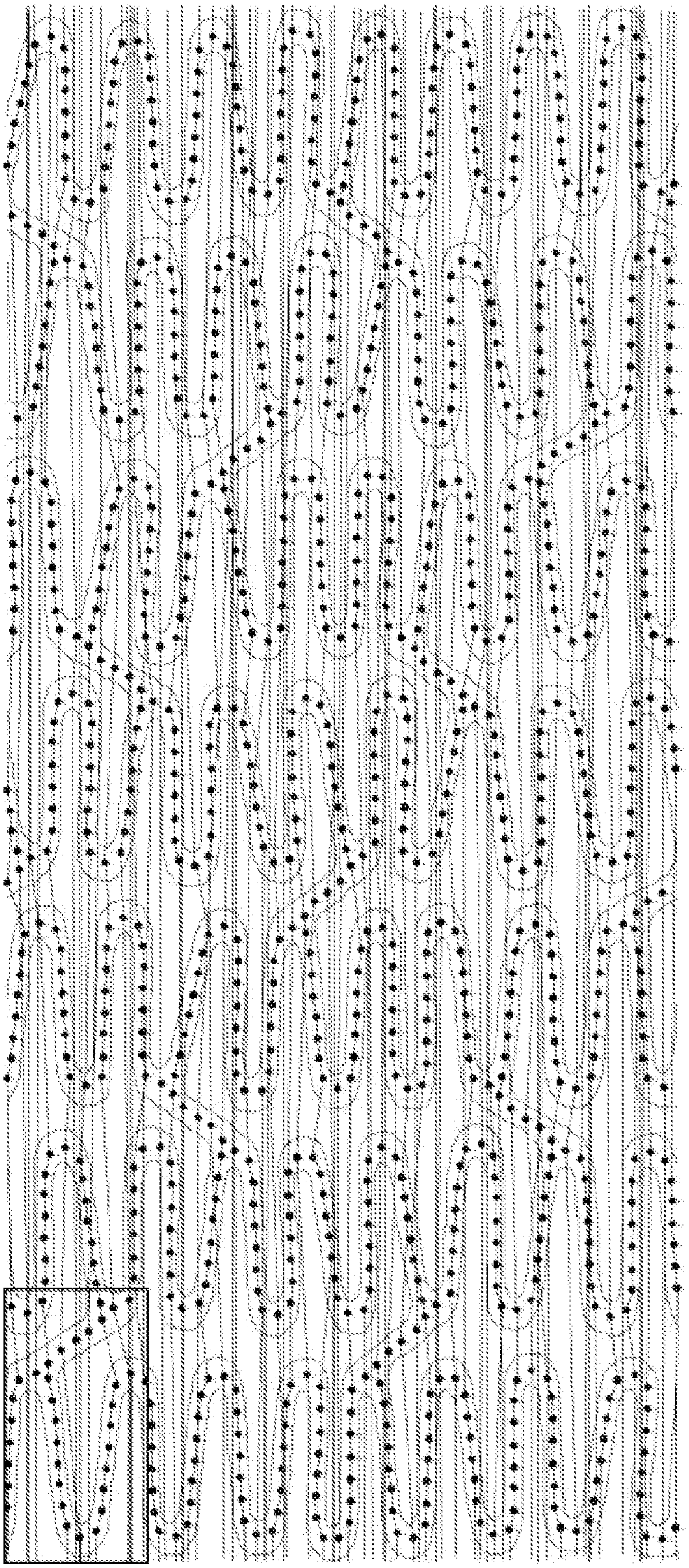

FIG. 16*a* is a representative example of the stent of FIG. 15 with a plurality of pathways formed by the algorithm shown in FIG. 13.

Figure 16B:
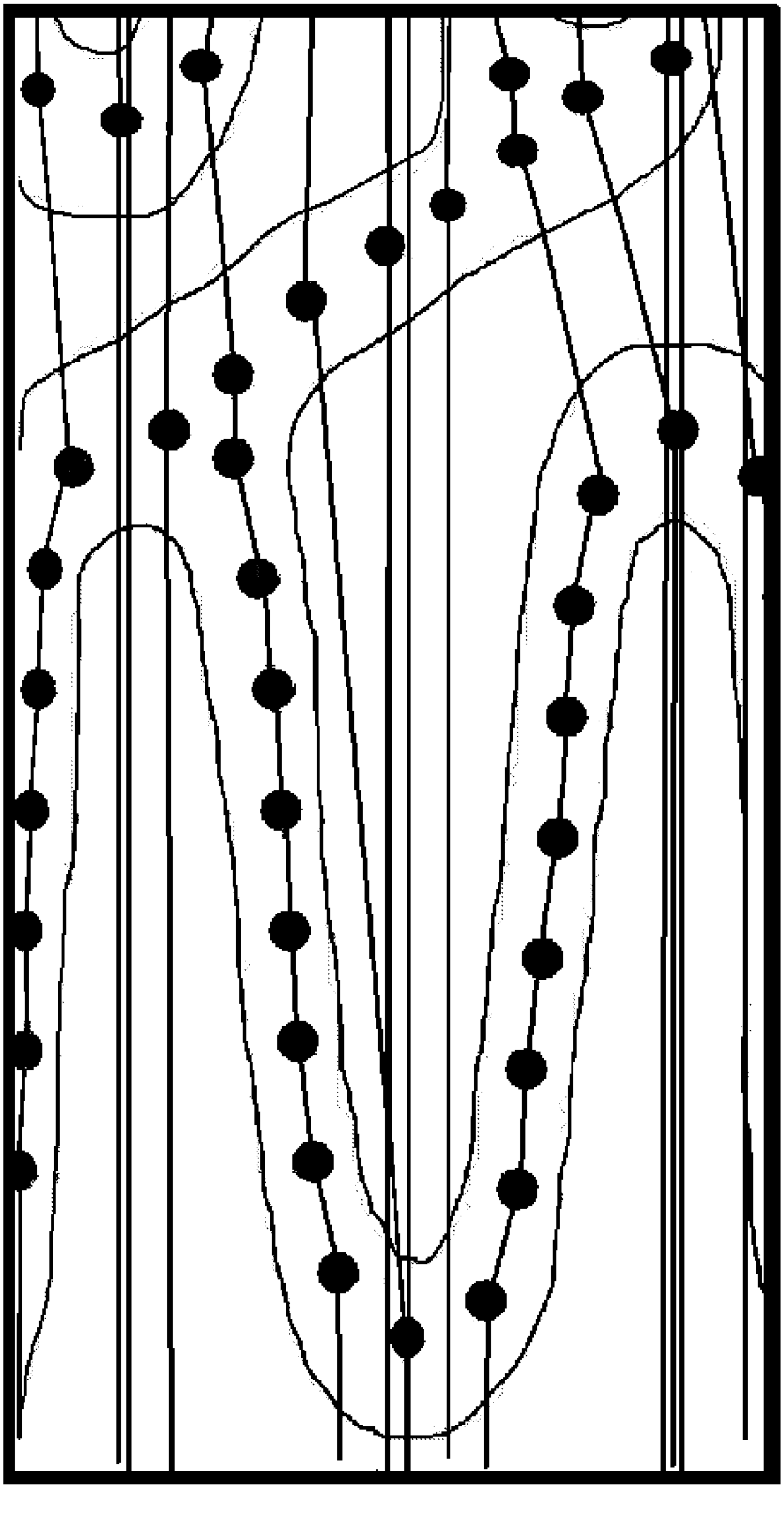

FIG. 16*b* is an enlargement of the boxed portion of FIG. 16*a*.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

For simplicity, "first end" as used in this application refers the left end of the stent pattern in the figures and "second end" as used in this application refers to the right end of the stent pattern in the figures. In some embodiments, the first end is the proximal end of a stent and the second end is the distal end of the stent and in other embodiments, the first end is the distal end of a stent and the second end is the proximal end of the stent.

Figure 1A:
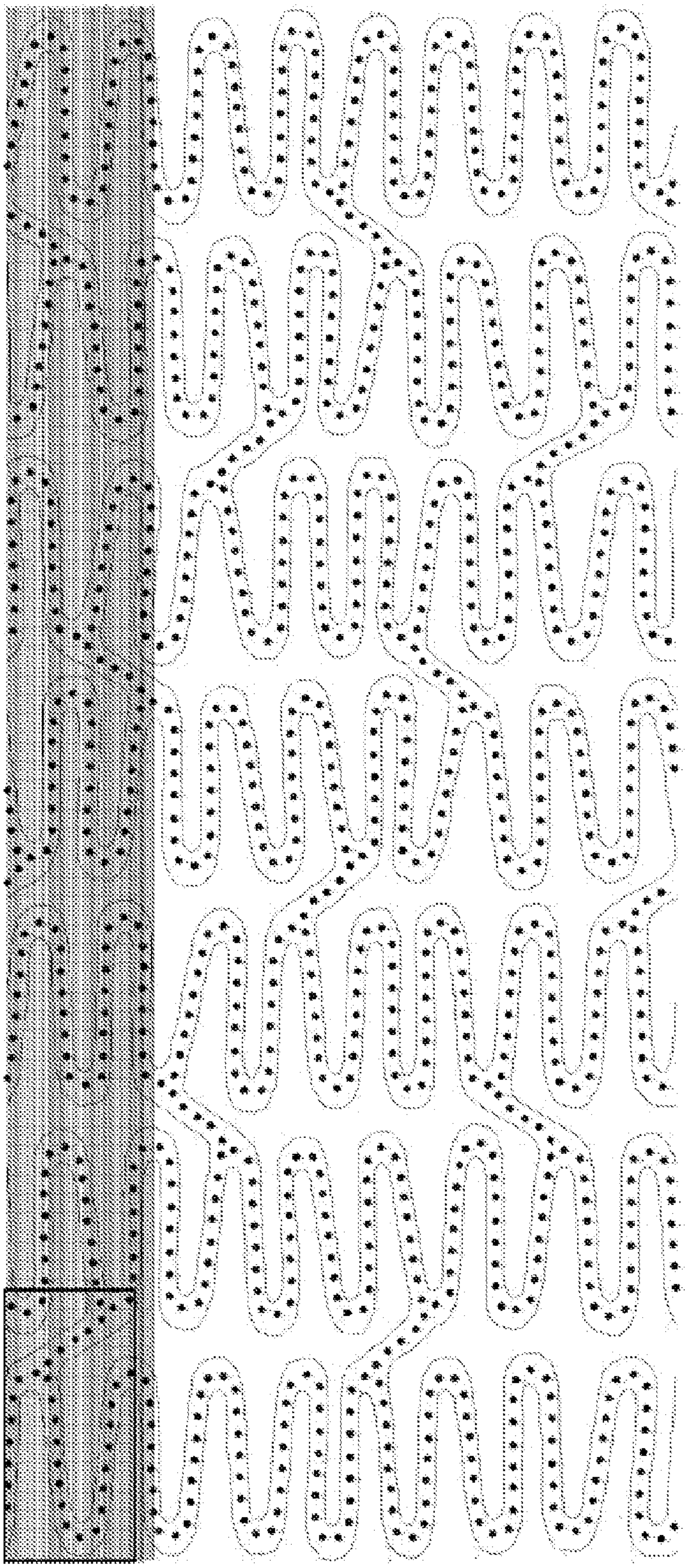
FIG. 1a PRIOR ART
Figure 1B:
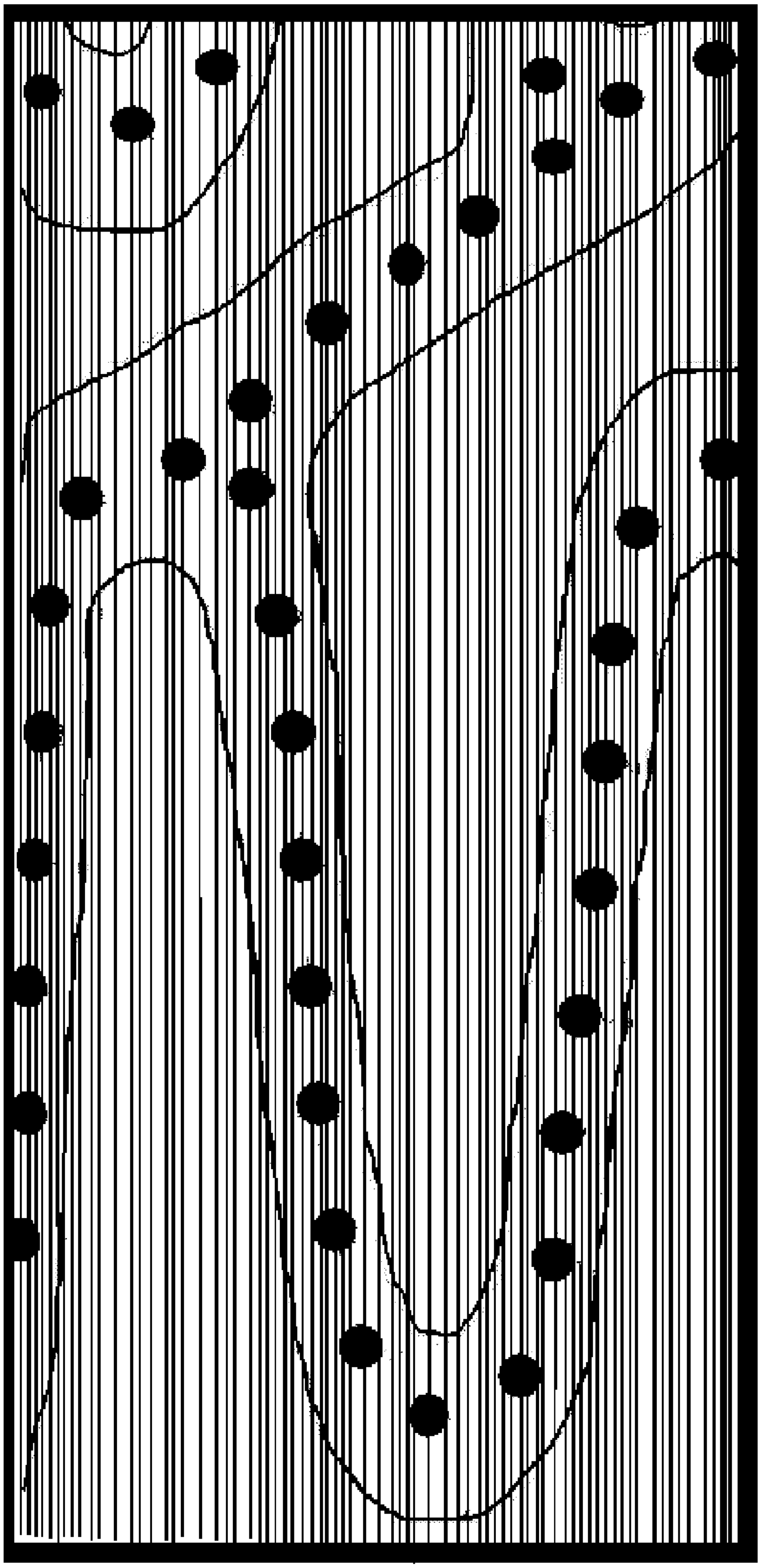
Figure 2:
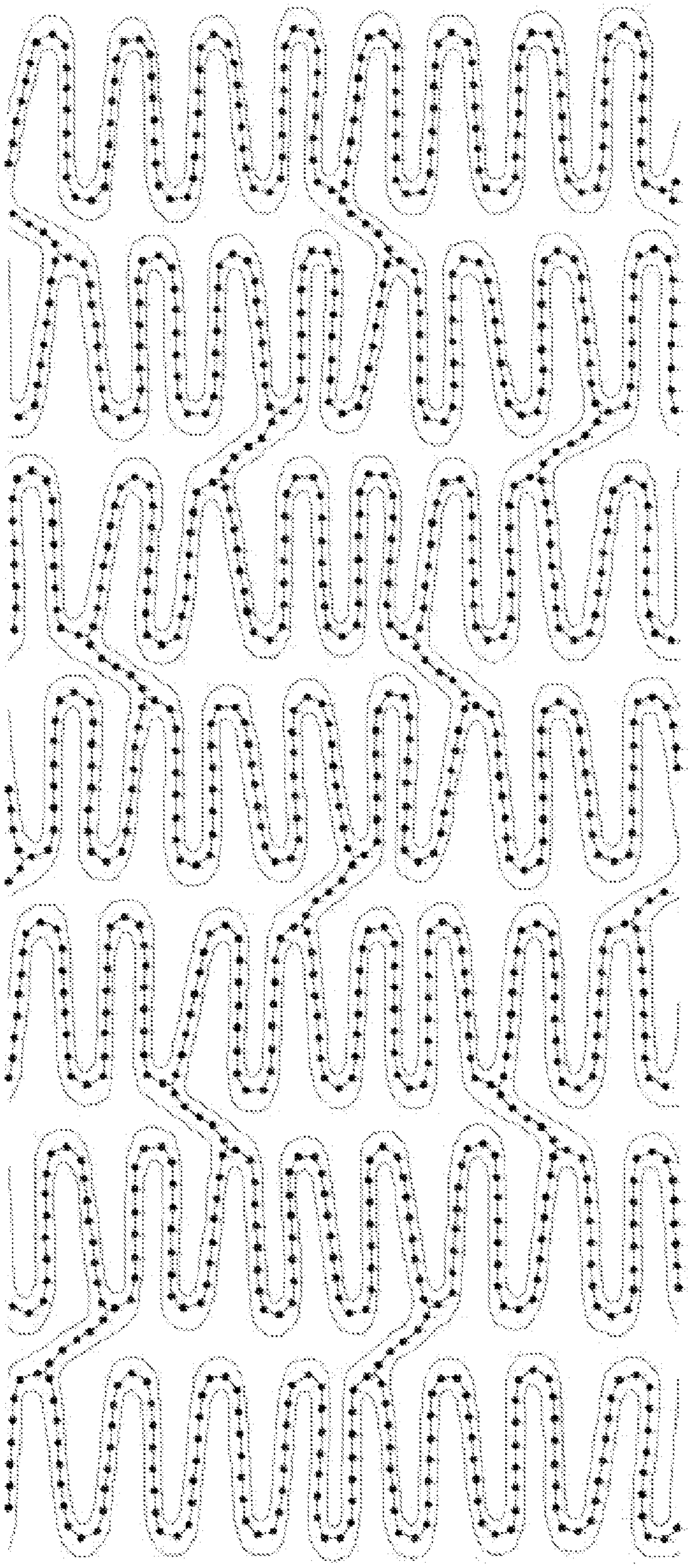
FIG. 2 PRIOR ART
FIG. 2 is shows a coating pathway determined by PRIOR ART vector coating.
Figure 3:
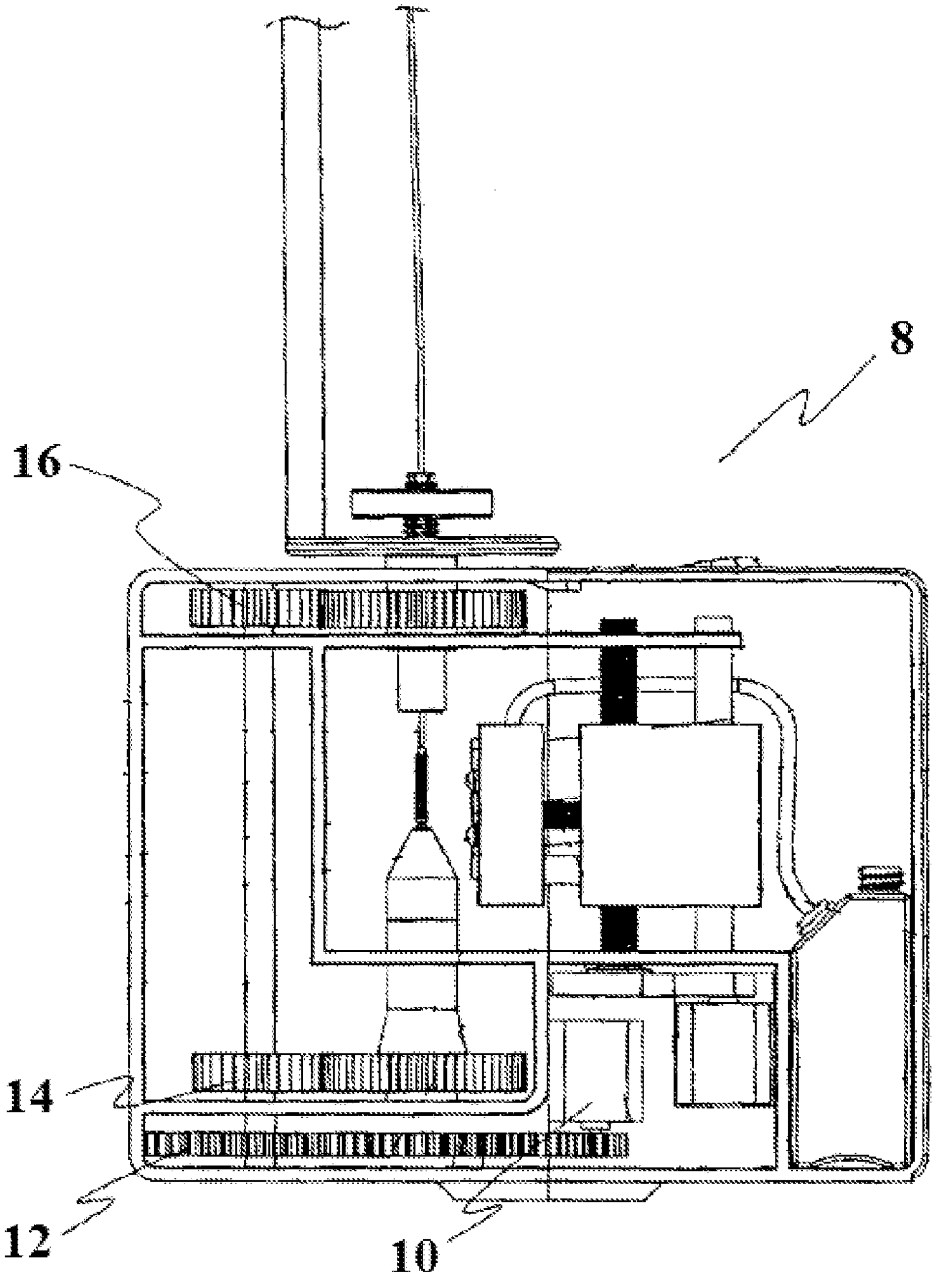
FIG. 3 PRIOR ART
FIG. 3 is an example of a PRIOR ART industrial premounted platform coating system.

In at least one embodiment, the method is directed to depositing coating material on a plurality of coating points on a surface of a medical device or medical prosthesis. Any suitable device or coating system can be used to deposit the coating material onto the medical device. For simplicity, a coating applicator will be used herein for the device or coating system. A non-limiting example of a suitable coating device is an Industrial Pre-Mounted Platform (IPMP) coating system. FIG. 3 is a non-limiting prior art example of an industrial Pre-Mounted Platform coating system as disclosed in U.S. Pat. No. 7,048,962 assigned to Boston Scientific Scimed, Inc., the entire contents of which is incorporated by reference in its entirety. Other configurations for a coating system are also contemplated.

In at least one embodiment, the drive motor and gearing/drive of the coating system are modified to alter the gear ratios for the rotation of the medical prosthesis. Different gear ratios alter the ability of the axis to rotate and to accelerate at higher rates. In at least one embodiment, the gear ratios of the motor 10 and the gear clusters 12, 14, 16 of the coating system shown in FIG. 3 are modified. For example, if the gear of the motor is modified to have more teeth than the gear clusters 12, 14, 16 the rotation of the gear clusters would increase thereby increasing the rotational speed of the stent for the exemplary coating system shown in FIG. 3.

It is within the scope of the invention for the coating material to be any suitable coating material, including but not limited to therapeutic agents, polymers, radiopaque materials, and any combinations thereof A non-limiting list of suitable therapeutic agents is provided below. Examples of medical devices or medical prostheses on which coating material can be deposited include stents, stent-grafts, grafts, vena cava filters, expandable frameworks, catheters, balloons, and portions thereof For simplicity, the discussion below will focus on an expandable prosthesis such as a stent. However, the principles disclosed herein can be applied to any medical device or prosthesis. As is known in the art, a stent has an unexpanded state before implantation in a body cavity, a crimped state when the stent is crimped onto a catheter for delivery to a body lumen, and an expanded state after implantation in a body cavity. However, the principles discussed below in reference to a stent can be applied to other medical devices.

Figure 4:
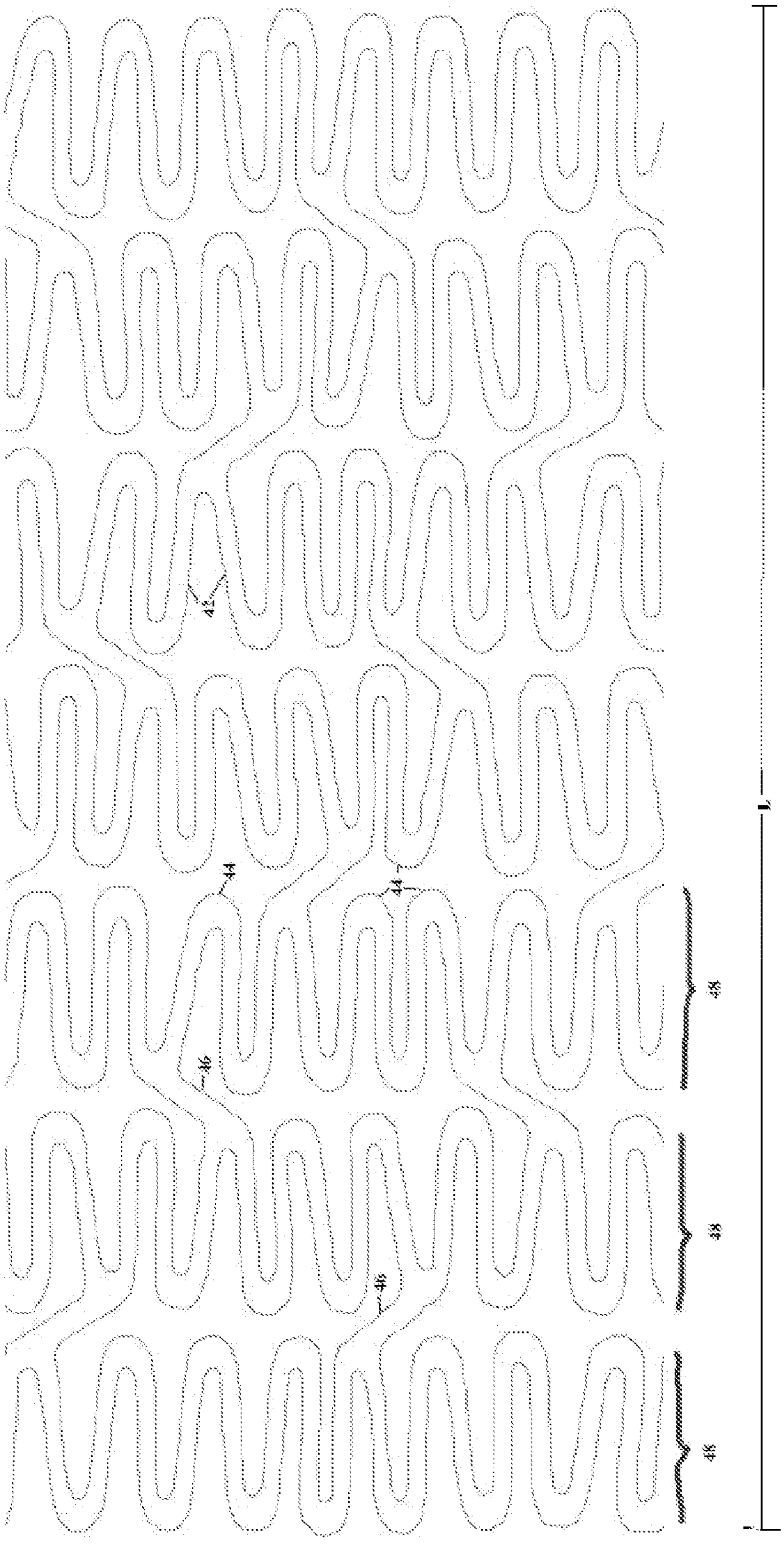
FIG. 4 is a flat view of a stent pattern.

As shown in FIG. 4, the stent includes a plurality of interconnected struts 42 that are arranged in a pattern. For comparison purposes the stent pattern in FIGS. 1-2, 4-5, 8-12, and 15-16 is the same pattern. In some stents the interconnected struts form circumferential bands, or circumferential rings, 48 that extend about the circumference of the stent. The struts 42 in a circumferential band or ring 48 are engaged one to another by turns 44. Adjacent circumferential bands 48 are engaged one to another by connectors 46. In some stents the struts 42 are substantially parallel to the longitudinal axis of the stent when the stent is in an unexpanded state. An exemplary stent and stent pattern with struts that are substantially parallel to the longitudinal axis of the stent (L) is shown in FIG. 4. Although a stent is substantially tubular when coating material is applied to the stent, for simplicity, the figures show a stent in flat view, as a stent map. A flat view is a view of a tubular stent that has been cut longitudinally from one end to another and laid out flat. In some embodiments, the stent is coated after it has been crimped onto a catheter or other suitable delivery device, i.e. when the stent is in a crimped state. In other embodiments, the stent is coated when it is in an un-crimped state, i.e. any state in which it is not crimped onto a balloon catheter or other suitable delivery device.

Figure 5:
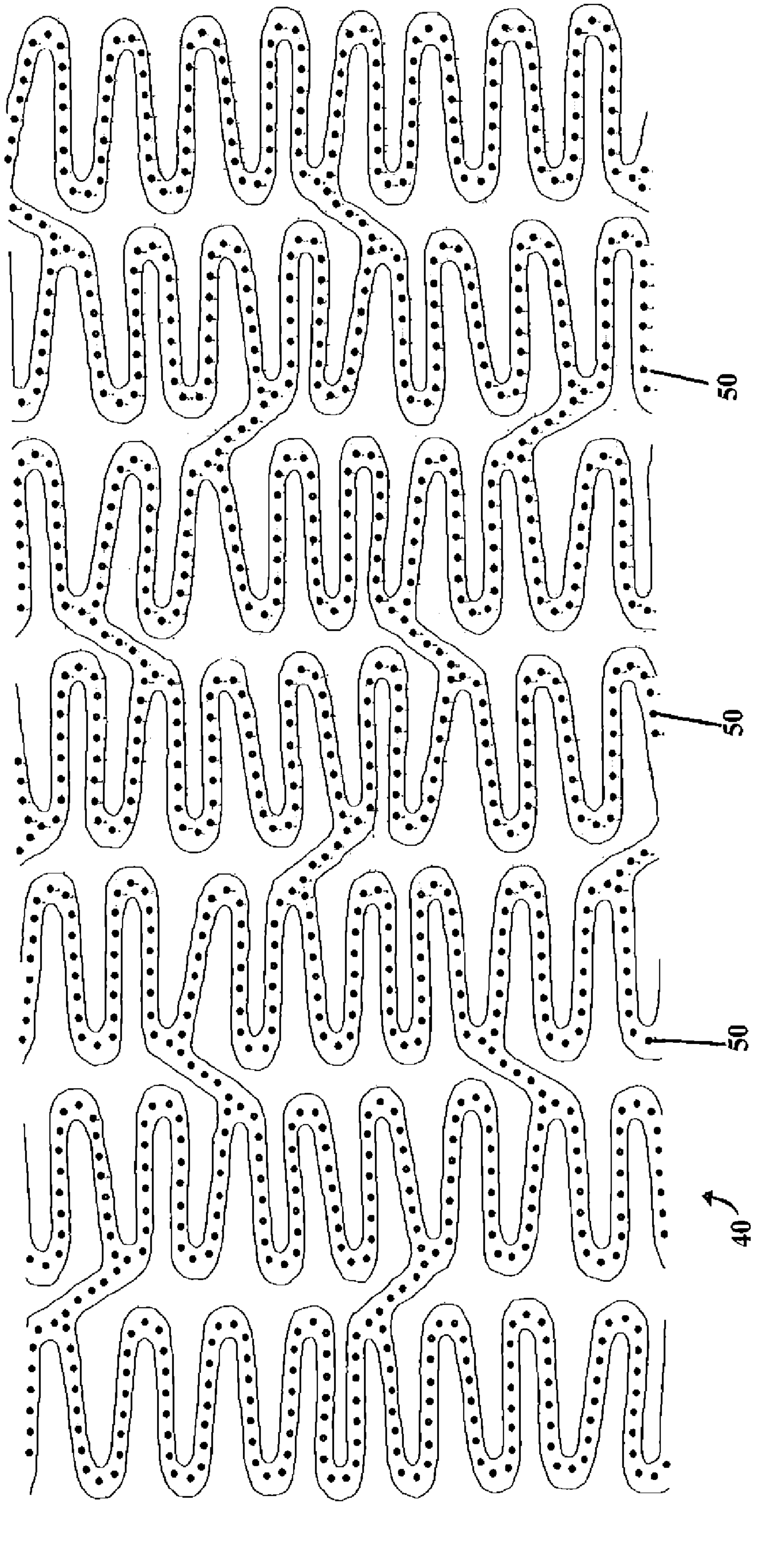
FIG. 5 is the stent pattern of FIG. 4 with coating points for coating material to be deposited.

The method of coating a stent begins with identifying locations on the stent at which coating material is to be deposited. These locations are coating points 50. To identify coating points, the stent, crimped or uncrimped, is pre-scanned by any suitable method to obtain an image of the stent which is then analyzed by any suitable method to determine the coating points for the stent. Suitable methods to determine coating points include scan algorithms and dot spacing. FIG. 5 shows coating points 50 identified for the stent of FIG. 4 with each coating point indicated by a circle. Once the coating points are identified, a plurality of pathways 52 are determined by an algorithm, as discussed below in greater detail. In at least one embodiment, each pathway 52 bisects at least one of the plurality of coating points 50 and extends from the one end of the stent to the other end of the stent.

In at least one embodiment the pathways 52 are determined by an algorithm which is run before a stent is coated. In some embodiments, the algorithm determines the pathways 52 in reference to the stent pattern. This algorithm can be considered a pattern based algorithm In one embodiment, the pattern based algorithm is used to determine pathways for stent patterns with struts that are substantially longitudinal to the longitudinal axis of the stent when the stent is in an unexpanded state. In at least one embodiment, the pattern based algorithm is embodied in computer code. In another embodiment, the algorithm determines the pathways 52 in reference to bands having a circumferential width. This algorithm can be considered a band algorithm. In at least one embodiment, the band algorithm is embodied in computer code.

In at least one embodiment, the algorithms described herein allow each pathway to be substantially longitudinal without requiring the pathway to be parallel to the longitudinal axis of the stent. In at least one embodiment, the center point of each coating point on a pathway is longitudinally separated from the center point of the adjacent coating point on the pathway. Thus the pathway progresses from one end of the stent to the other end of the stent along each travel path.

In at least one embodiment, the algorithm has a predetermined maximum amount of deviation relative to the longitudinal axis of the stent being coated. Although the maximum amount of deviation can be varied by the user based on the coating requirements, the larger the angular deviation, the larger the rotation of the stent which increases the coating time because time is lost if the rotation is excessive. Thus, a larger angular deviation equates to a larger rotation of the stent rotation axis and a longer coating time.

In some embodiments, each pathway 52 formed by the algorithms discussed herein has an overall variation of ± degrees relative to the longitudinal axis of the stent. One example of a pathway that has an overall variation relative to the longitudinal axis of the stent is a pathway with a first end having a first circumferential location and a second end having a second circumferential location that is different from the first circumferential location. Pathways with first and second ends that have different circumferential locations can be seen for example in FIGS. 7-8 and 14. In some embodiments, the variation between the first and second locations relative to the longitudinal axis is about ±3° to about ±9°. In other embodiments, the variation between the first and second locations relative to the longitudinal axis is about ±1° to about ±15°. For the stent pattern shown in the figures, the variation is about ±6°.

In other embodiments, each pathway 52 formed by the algorithms discussed herein comprises a plurality of travel paths, with each travel path connecting two coating points and extending at an angle relative to the stent axis that is no greater than a predetermined maximum amount of deviation. Thus, each travel path can have any angle relative to the longitudinal axis of the stent so long as it does not exceed the predetermined maximum amount of deviation. Pathways with travel paths that do not exceed a predetermined maximum amount of deviation can be seen for example in FIGS. 7-8, 14, and 16. In at least one embodiment, the user defined maximum angle of deviation is greater than 0° relative to the longitudinal axis of the stent. In some embodiments, the user defined maximum angle of deviation is about ±45°. In other embodiments, the user defined maximum angle of deviation is about ±30°. In still other embodiments, the user defined maximum angle of deviation is about ±20°. As discussed above, each user defined maximum angle of deviation includes any angle up to the user defined maximum angle of deviation.

In at least one embodiment, the pattern of the stent and the performance capabilities of the coating system used to coat the stent affect the overall variation of ± degrees relative to the longitudinal axis of the stent and affect the predetermined maximum amount of deviation. Performance capabilities of a coating system include rotational speed and acceleration. Thus for example, a method used with a coating system that has greater rotational performance can have a greater predetermined maximum amount of deviation than a method for a coating system with a lower rotational performance.

Figure 6:
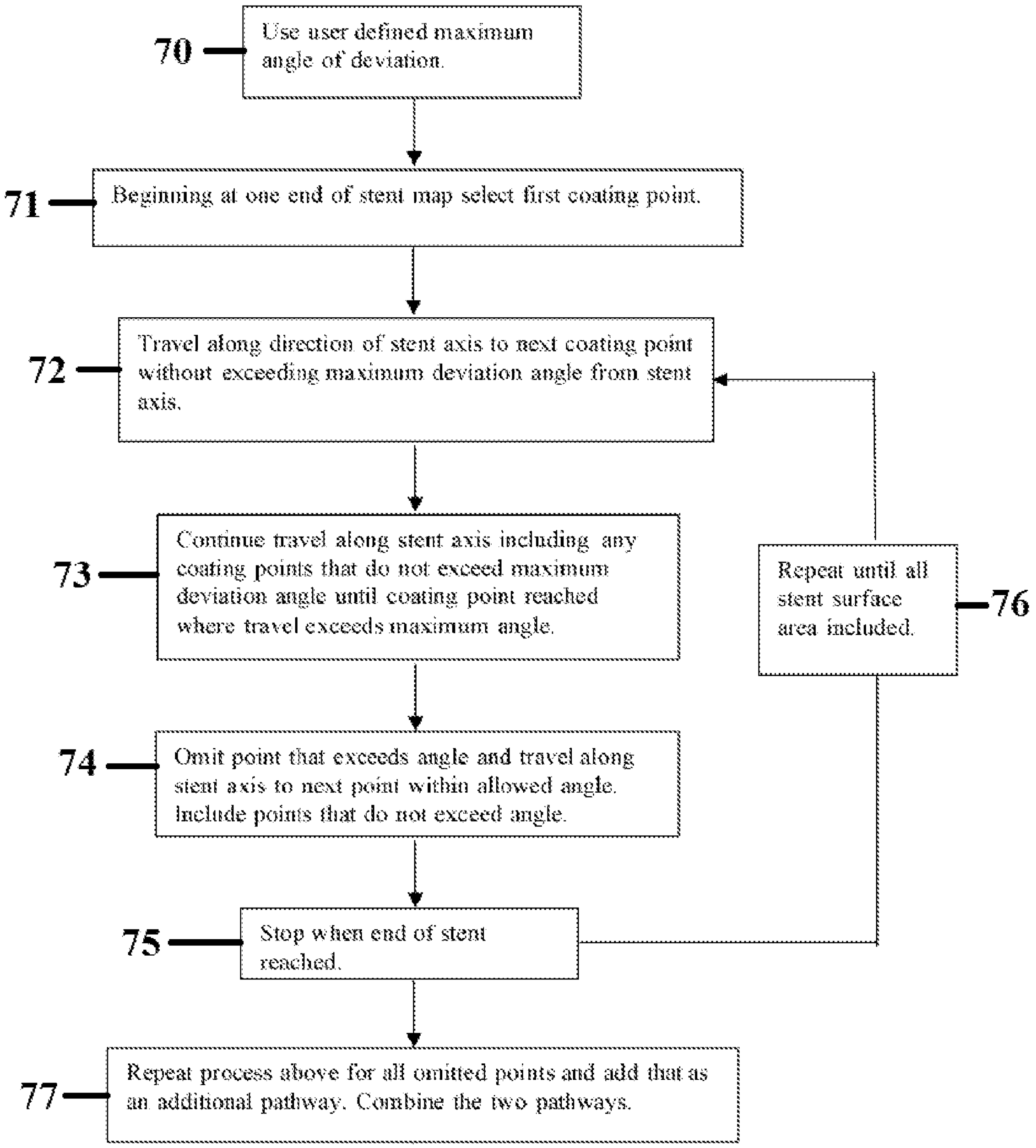
FIG. 6 is a flowchart of an algorithm to determine coating pathways.
Figure 7:
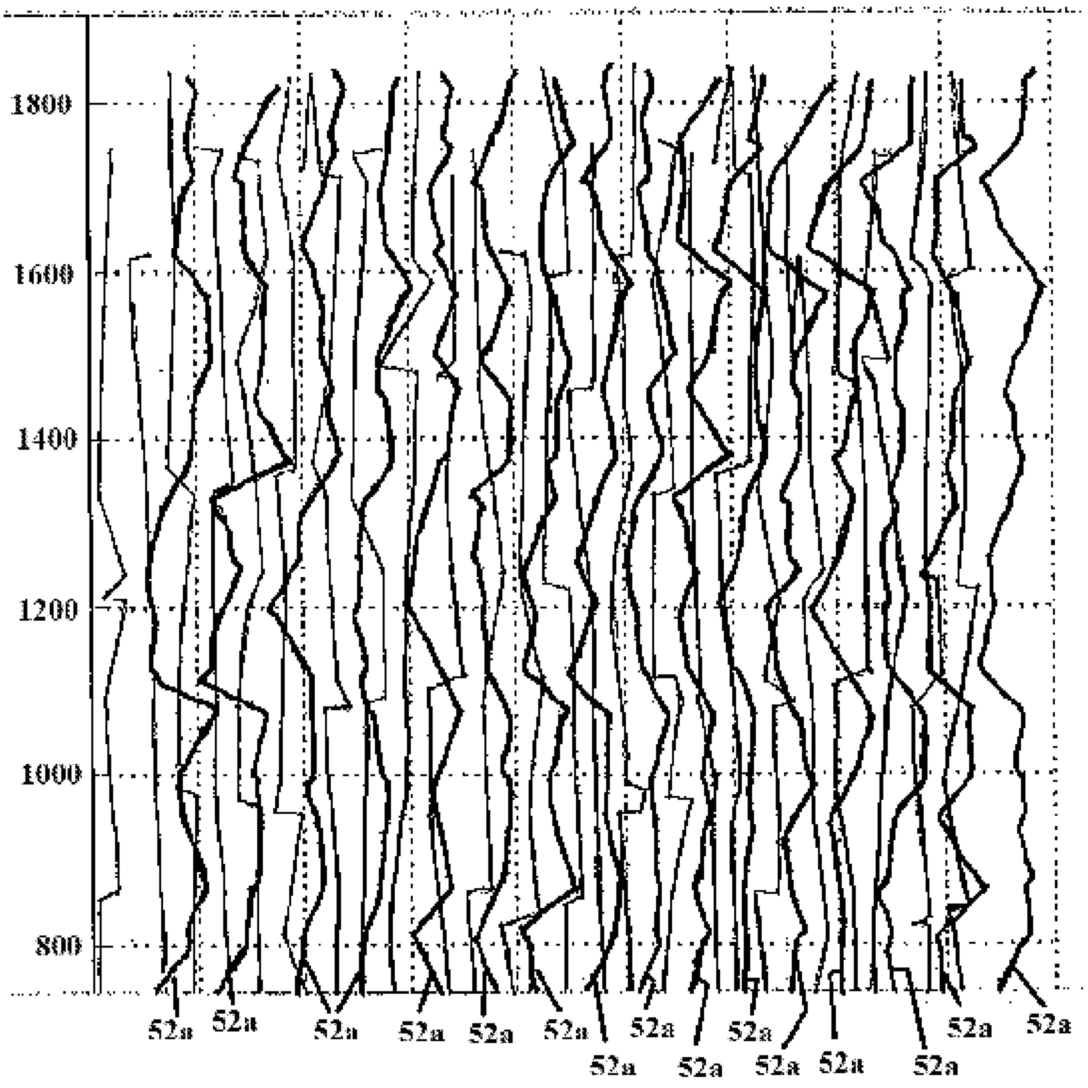
FIG. 7 is a graphical schematic of a stent pattern showing first pathways and second pathways determined by the algorithm represented by the flowchart of FIG. 6.
Figure 8:
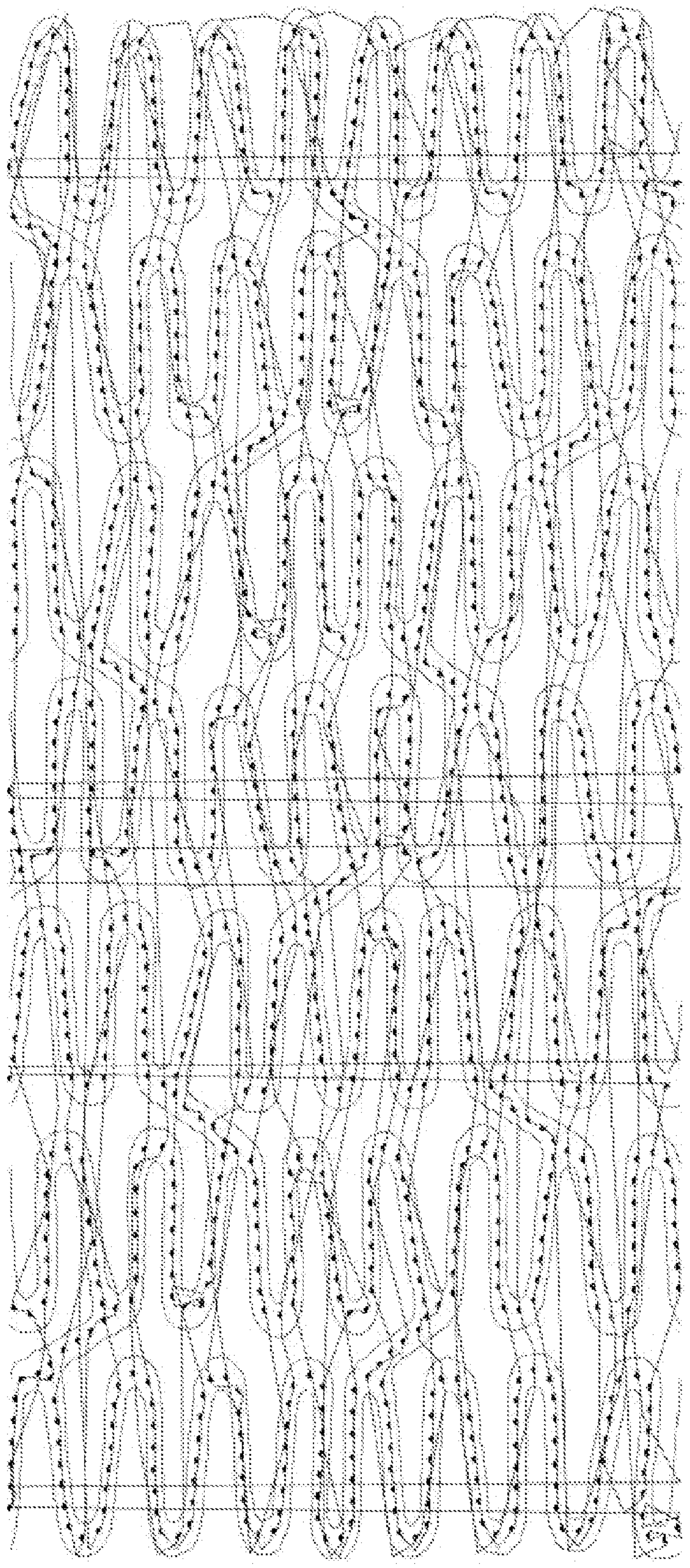
FIG. 8 is a representative example of the stent pattern of FIG. 4 with a plurality of pathways determined by the algorithm of FIG. 6.

The pattern based algorithm is a hybrid of raster coating and vector coating because angular limits that are predetermined are utilized to assign coating points to a pathway 52 and the pathway 52 is a vector path interconnecting the assigned coating points. FIG. 6 is a flowchart that schematically describes the steps of the method being performed by the pattern based algorithm (steps 70-77). FIG. 7 is a schematic graphical representation of the pathways determined by the pattern based algorithm. In FIG. 7, the longitudinal axis of the stent is the y-axis and the circumference of the stent is the x-axis. FIG. 8 shows the stent pattern of FIG. 4 with a plurality of pathways determined by the pattern based algorithm.

The first step of the method performed by the pattern based algorithm is to determine at least one user defined maximum angle of deviation from the longitudinal axis of the stent (step 70). Next, a first coating point is selected at a first end of the stent map (step 71). From the selected first coating point, the pathway 52 travels along the longitudinal axis of the stent to the next coating point without the pathway exceeding the user defined maximum angle of deviation (step 72). The pathway 52 continues along the axis of the stent connecting coating points that do not exceed the user defined maximum angle of deviation until a coating point that exceeds the user defined maximum angle of deviation is reached (step 73). The coating point that exceeds the user defined maximum angle of deviation is excluded from the pathway 52 and the pathway 52 continues along the stent axis to the next coating point that is within the user defined maximum angle of deviation so that the angle between two adjacent coating points on the pathway does not exceed the user defined maximum angle of deviation The result is that all the points on the pathway do not exceed the user defined maximum angle of deviation to the stent axis (step 74). The pathway ends at the second end of the stent map (step 75). Steps 72-75 are repeated until the entire stent surface has been covered (step 76). The pathways obtained from steps 72-76 can be considered to be first pathways 52*a*. After all the stent surface has been covered, steps 72-76 are repeated with the coating points that were excluded from the first pathways until all the coating points are on a pathway (step 77). The pathways with the excluded coating points can be considered to be second pathways 52*b*.

Figure 11:
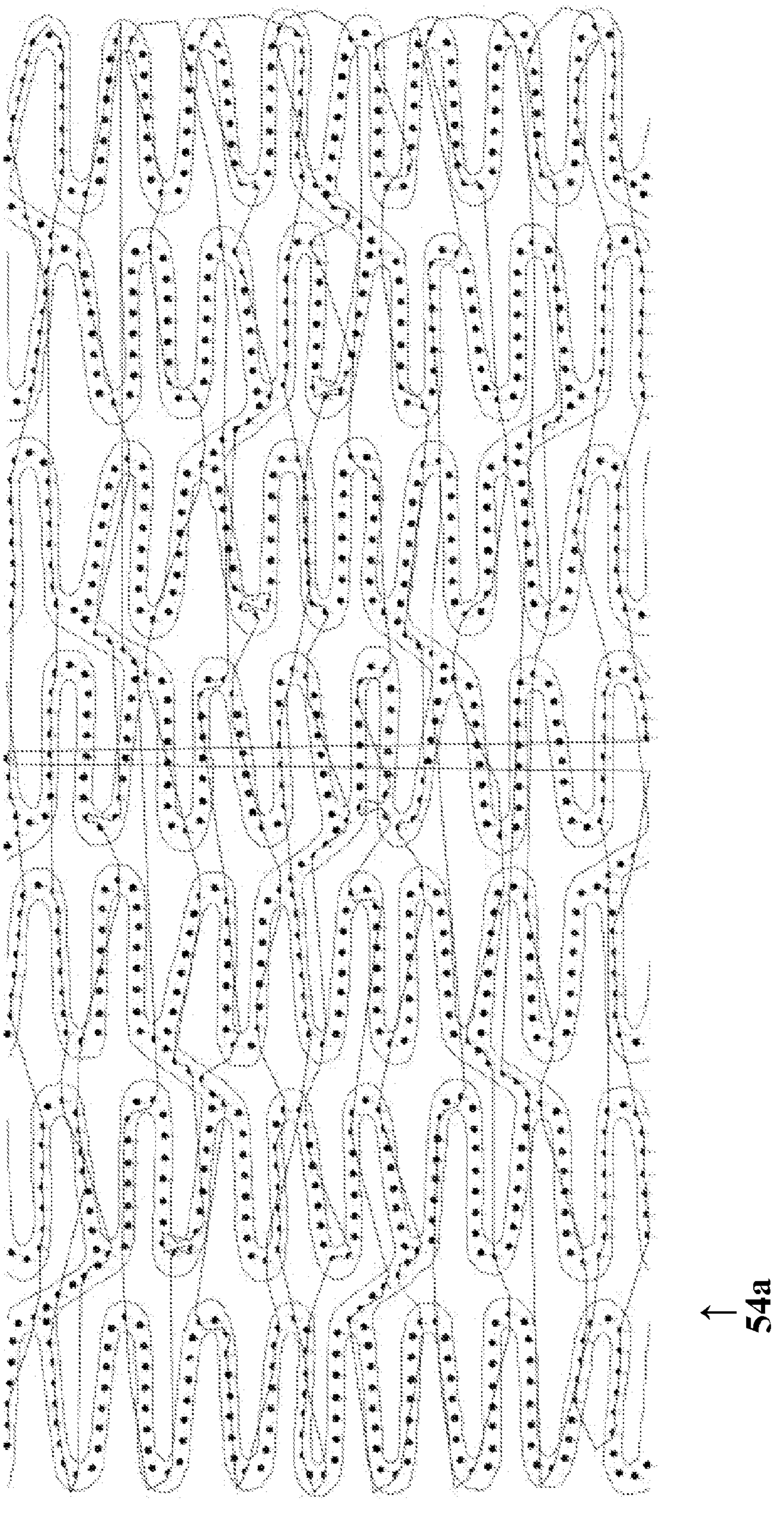
FIG. 11 shows the first portion of the coating pathway of FIG. 8.
Figure 12:
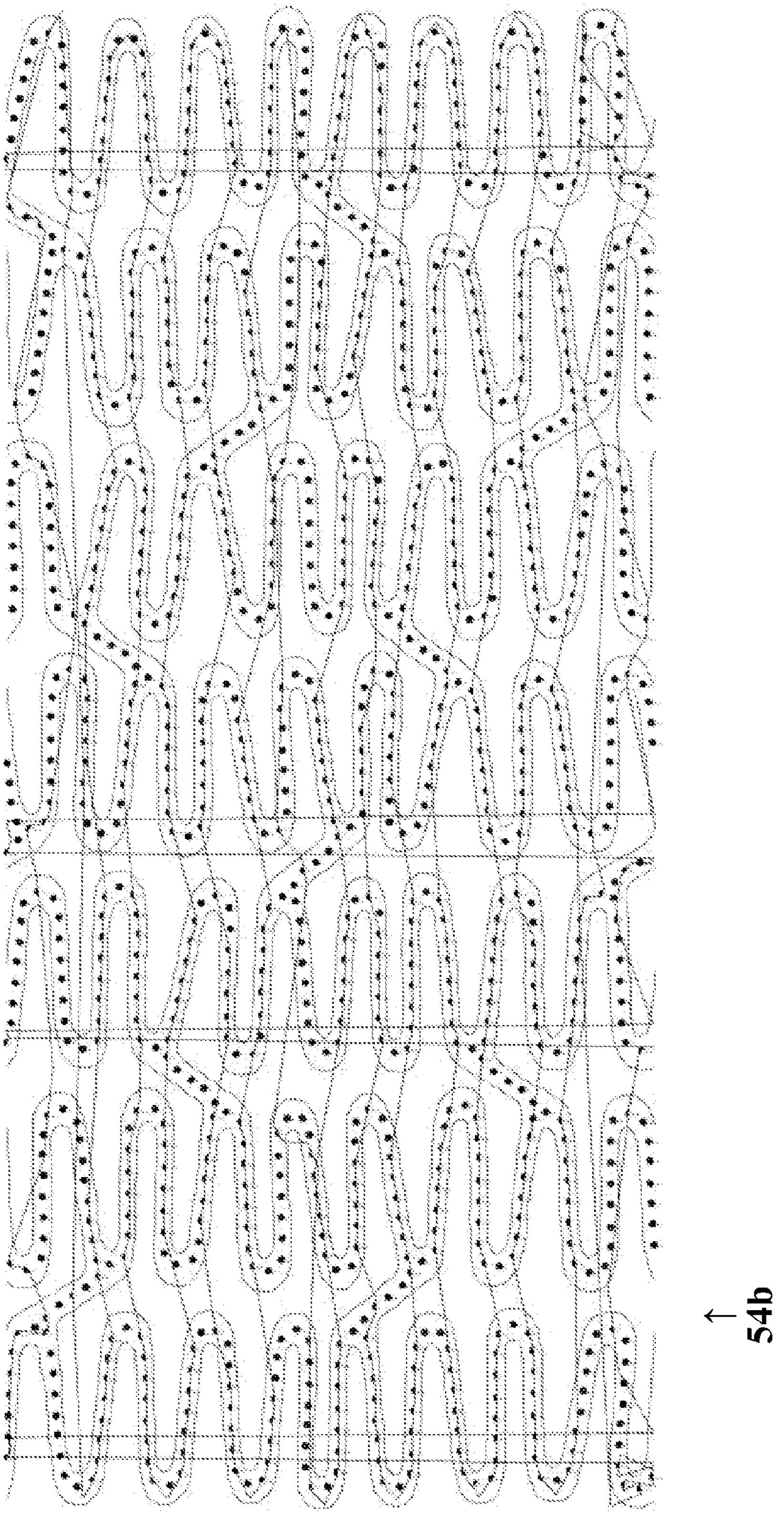
FIG. 12 shows the second portion of the coating pathway of FIG. 8.

After all the pathways are determined, the pathways 52 are linked together to form a coating pathway 54 along which the coating applicator will travel and deposit coating material onto each coating point. In some embodiments, the pathways 52 are linked end to end to form a single continuous coating pathway. In other embodiments, the pathways 52 are linked end to end to form a plurality of coating pathways. A continuous coating pathway allows the coating applicator or coating system to move continuously while depositing coating material onto each coating point. In some embodiments, the coating pathway 54 has a first portion 54*a* that travels in a first circumferential direction about the circumference of the stent and a second portion 54*b* that travels in a second circumferential direction, opposite to the first circumferential direction. This shown for example in FIGS. 11 and 12. FIG. 11 shows a first portion of the coating pathway 54*a* that begins with pathway 0 and continues through pathway 16, and FIG. 12 shows the second portion of the coating pathway 54*b* that beings with pathway 17 and continues through pathway 33. Thus, a coating applicator, traveling along the coating pathway shown in FIGS. 11-12, travels around the entire circumference of the stent in one direction and then travels around the entire circumference of the stent in the opposite direction. This coating pathway 54 can be considered to have a portion (s) that extends in an opposite direction about the circumference relative to the previous portion.

In other embodiments, the coating pathway 54 extends only in a first circumferential direction about the circumference of the stent being coated. In this embodiment, the end of pathway 17, shown as being connected to pathway 18 in FIG. 12, would instead be connected to the end of pathway 33. This pathway would begin at pathway 0 and continues through pathway 17 then continues at the beginning of pathway 33 and extends along pathways 32 to 19 to the end of pathway 18.

Thus, a coating applicator, traveling along this coating pathway would travel two times around the circumference of the stent being coated.

In at least one embodiment, the pattern based algorithm further comprises determining a coating time for the coating pathway obtained in step 77. In some embodiments, the pattern based algorithm further comprises repeating steps 70-77 with additional predetermined maximum angles of deviation in addition to the first predetermined maximum angle of deviation; determining which coating pathway has the lowest coating time; and then coating the stent using the coating pathway with the lowest coating time.

After a coating pathway is determined by either of the methods described above, the method of coating further comprises coating the medical device. As discussed above, examples of medical devices or medical prostheses on which coating material can be deposited include stents, stent-grafts, grafts, vena cava filters, expandable frameworks, catheters, balloons, and portions thereof In at least one embodiment, the stent is coated using the coating pathway with the lowest coating time. It is within the scope of the invention for the coating applicator to travel along the coating pathway more than one time.

In at least one embodiment, the pattern based algorithm assigns a greater value to coating points on the struts than to coating points on the turns and the connectors. For example, coating points on a strut are each assigned a first value and coating points on a connector or a turn are each assigned a second value that is less than the first value. In this method, the first coating point that is selected is a coating point that has been assigned the first value. In some embodiments, this results in two pathways: first pathways 52*a* which connect most of the coating points 50 on the struts and a few of the coating points on the turns and connectors and second pathways 52*b* which connect points that were not connected by the first pathways. This is shown graphically in FIG. 7. In other embodiments, assigning a value to coating points is used to filter the coating points. For example, if coating material is desired only on coating points located on struts and not the turns, the coating points located on the struts are given a first value and the coating points located on the turns are given a second value and the algorithm assigns only coating points with a first value to a pathway.

Alternatively, if more than one type of coating material is to be deposited onto the stent, coating points onto which a first coating material is to be deposited are assigned a first value and coating points onto which a second coating material is to be deposited are assigned a second value and each pathway connects only coating points having the same value.

FIG. 8 shows the stent pattern of FIG. 4 with an example of a plurality of pathways determined by the pattern based algorithm. Because the plurality of pathways depend upon variables such as stent pattern and the maximum angle of deviation that is used, FIGS. 8-12 are representative examples of pathways that can be generated by the pattern based algorithm. As shown in FIGS. 8-12, there are several instances where the coating pathway extends from the bottom of the stent map to the top of the stent map and therefore appears to travel at an angle close to 90 relative to the longitudinal axis of the stent as it travels from one coating point to another. However, this is a result of the tubular stent being represented as a flat stent map. Thus, the coating points at the top of the stent map are close to the coating points at the bottom of the stent map.

Figure 9:
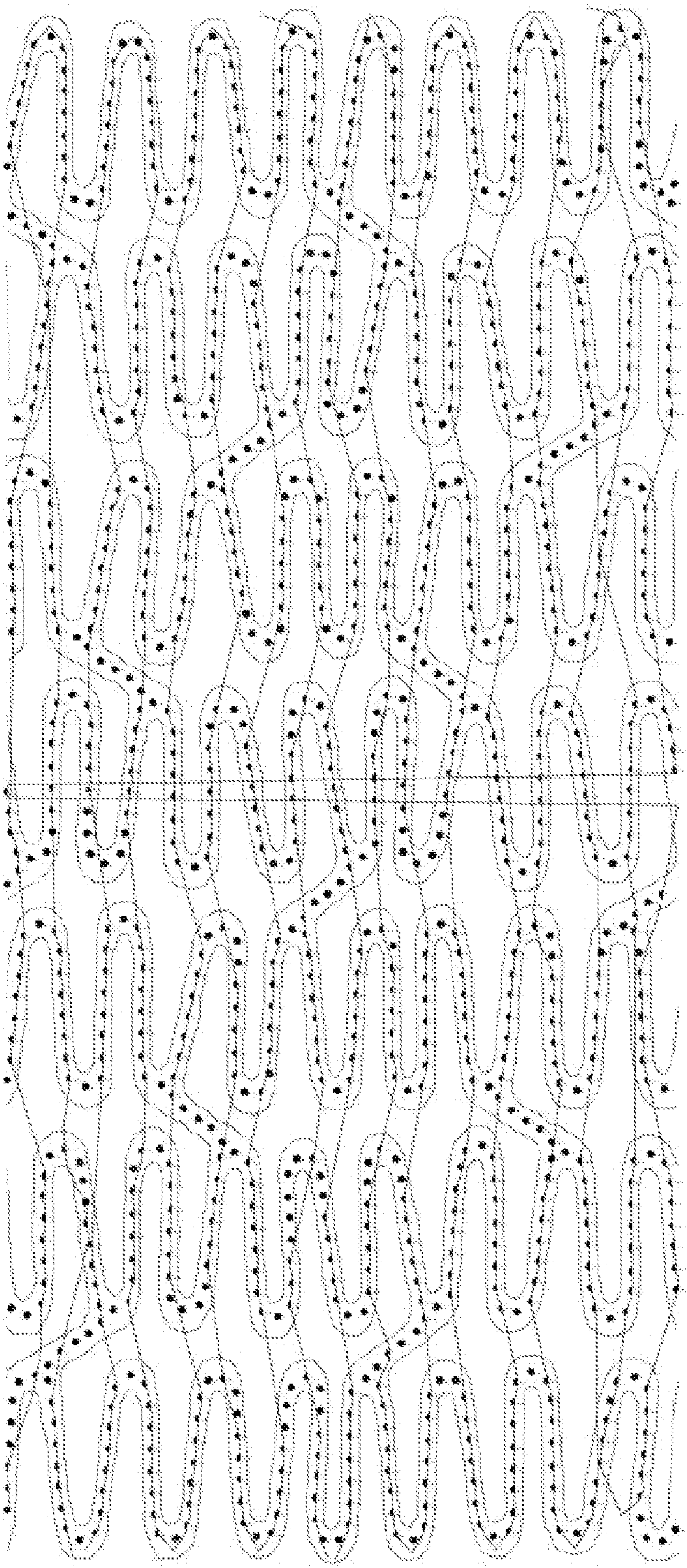
FIG. 9 shows only the first pathways of FIG. 8.
Figure 10:
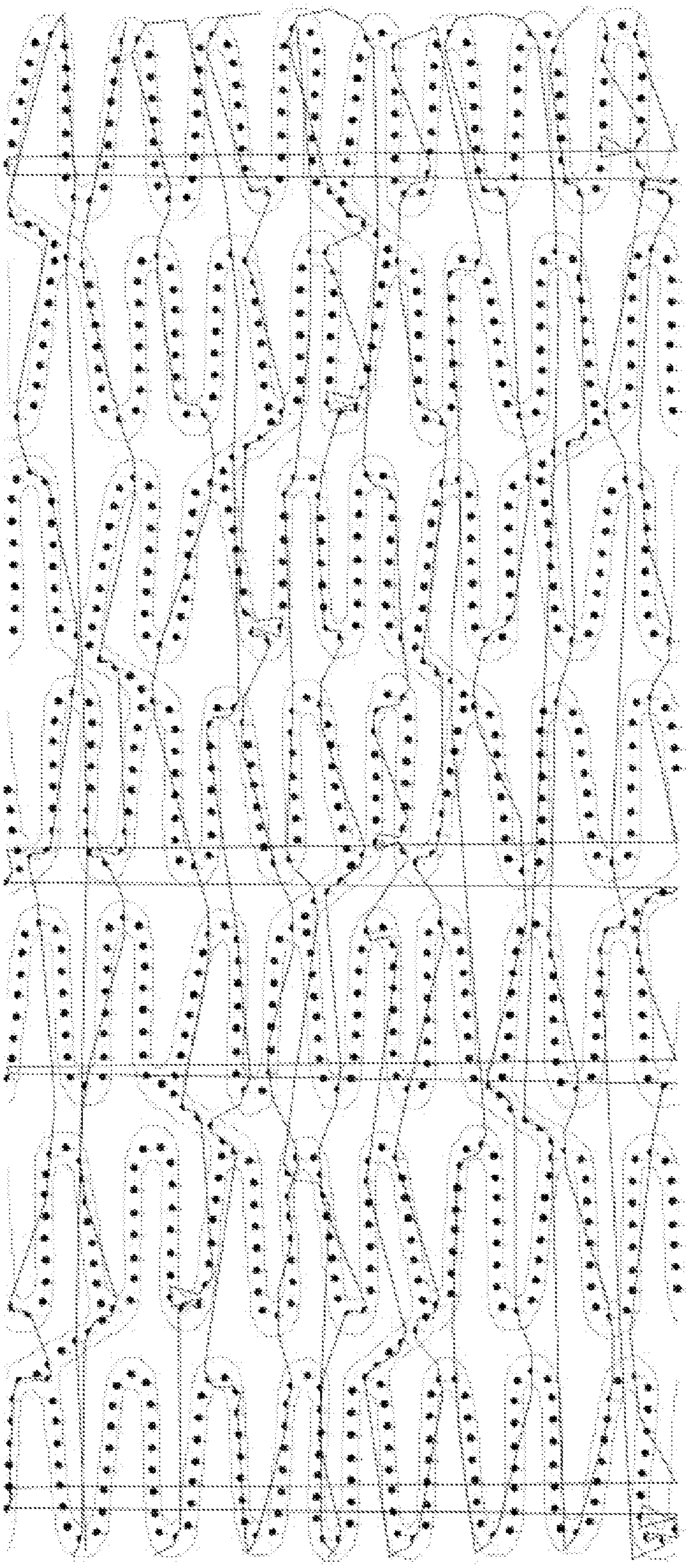
FIG. 10 shows only the second pathways of FIG. 8.

FIGS. 9-10 show the stent of FIG. 8 with pathways 52, numbered 0-33, that were determined using the pattern based algorithm. Hereinafter pathways shown in FIGS. 9-11 will be identified according to the pathway number, e.g. pathway 0. As can be seen from FIGS. 9-10, the first pathways 52*a*, shown in FIG. 9, primarily bisect coating points positioned on the struts whereas the second pathways 52*b*, shown in FIG. 10, primarily bisect coating points positioned on the turns and the connectors.

In at least one embodiment, each pathway 52 extends a slight distance beyond the end of the stent so that the ends of two pathways can be connected to form a part of the coating pathway. Note that connected pairs of pathways 52 have ends that are circumferentially separated from one another so that the coating applicator can progressively move around the circumference of the stent along the coating pathway 54. For example, as can be seen in FIG. 11, the first end of pathway 0 is circumferentially separated from the first end of pathway 1.

As can be seen in FIG. 11, some of the pathways overlap one another and some pathways extend through the same coating point. As discussed above, only the pathway that bisects the coating point is the pathway along which the coating applicator deposits coating material at that location. When the coating applicator is on a pathway that extends through a portion of the coating point but does not bisect the coating point, the coating applicator does not deposit coating material at that location. For reference in the figures, each coating point that is bisected by a pathway is partially shaded and each coating point that is not bisected by a pathway is entirely shaded. The shading of the coating points is merely an aid to identify coating points which are bisected by one of the pathways shown in the figure relative to coating points that are not bisected by a pathway.

Figure 14:
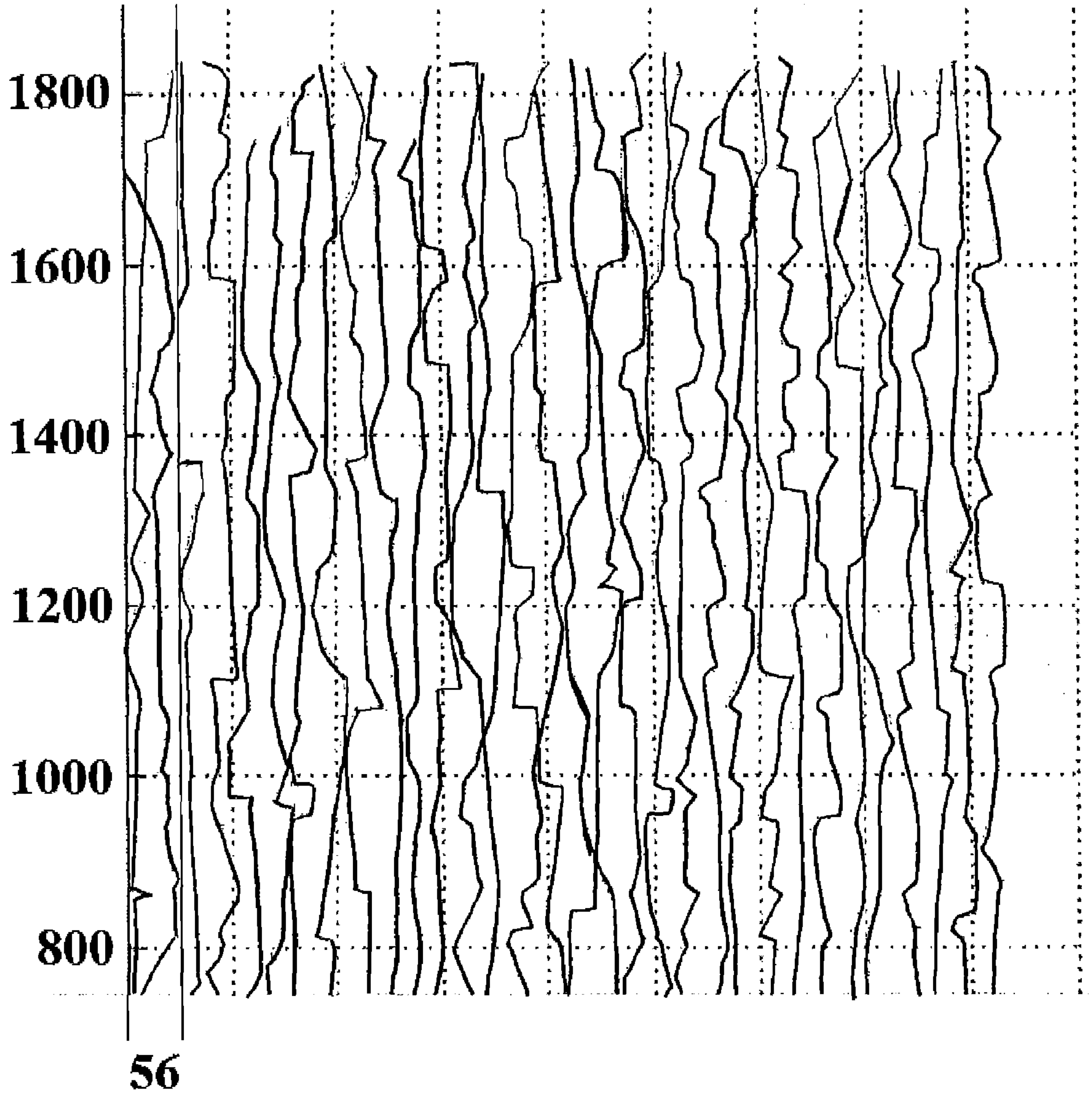
FIG. 14 is a graphical schematic of pathways determined by the band algorithm represented by the flowchart of FIG. 13.

The band algorithm is a hybrid of raster coating and vector coating because band and angular limits that are predetermined are utilized to assign coating points to a pathway, and the pathway 52 is a vector path interconnecting the assigned coating points based on the predetermined band width and angular limit FIG. 13 is a flowchart that schematically describes the steps of the method being performed by the band algorithm. FIG. 14 is a graphical schematic of pathways determined by the band algorithm. In FIG. 14, the longitudinal axis of the stent is the y-axis and the circumference of the stent is the x-axis. FIG. 15 shows a stent pattern divided into a plurality of bands 56*a-n*. FIG. 16*a* is a representative example of a plurality of pathways determined by the band algorithm for the stent of FIG. 15. FIG. 16*b* is an exploded view of the portion of FIG. 16*a* bounded by the box (upper left corner). Note that depending on the user defined maximum deviation from the longitudinal axis of the stent, the pathways can be different from those shown in FIG. 16*a* for this particular stent pattern. As discussed above, the stent pattern is one variable that affects the pathways generated by the algorithms disclosed herein.

Each pathway 52 formed by the band algorithm has an overall variation of ± degrees relative to a straight longitudinal line and has portions which extend at an angle no greater than the maximum amount of deviation relative to the longitudinal axis of the stent. In at least one embodiment, the center point of each coating point on a pathway is longitudinally separated from the center point of the adjacent coating point on the pathway. Thus the pathway progresses from one end of the stent to the other end of the stent along each travel path.

As shown by the flowchart, the first step of the band algorithm is to divide the stent into bands that have a width equal to the lowest value of a user selected range, a nominal initial value (step 80). In at least one embodiment the nominal initial value is the at least equal to the width of the struts. In some embodiments, some coating points are positioned in two adjacent bands so that a portion of the coating point is positioned within one band and a portion of the coating point is positioned within another band, as shown in FIG. 15. Sometimes a greater percentage of the coating point is within one band than the other band. In this case the coating point is assigned to the band in which the larger portion is positioned. Other times the coating point is evenly distributed between the two bands. In this case, the assignment of the coating point to a band depends on its position relative to adjacent coating points and the coating point is assigned to the band in which the coating point can be assigned to a coating pathway fulfilling the criteria. In other embodiments, each coating point in positioned entirely within a single band. This can occur for example in a digital system where each coating point is a pixel and therefore is positioned entirely within a single band.

The next step is to assign the coating points in each band to a pathway, omitting any coating point that requires a deviation greater than the maximum angle of deviation from the pathway (step 81). The user determined maximum deviation for the pathways shown by the representative example of FIG. 16*a* is about ±20°. Next, the omitted coating points in each band are assigned to at least one pathway 52 (step 82). Thus, each longitudinal band has at least one pathway, as can be seen in FIG. 14 by band 56 as well as in FIG. 16*a*. A coating pathway 54 is formed by linking or connecting these pathways 52 (step 83). Note that the pathways shown in FIG. 16*a* have not been linked to form a coating pathway. Next, the coating time for the coating pathway 54 is calculated (step 84). The increment width value for the bands in increased and steps 80-84 are repeated until the maximum width value has been used (step 85). The coating times for each width value are compared and the width value that results in a coating pathway with the lowest coating time is determined (step 86).

After a coating pathway with the lowest coating time is determined, the method of coating further comprises coating the medical device using the coating pathway with the lowest coating time. As discussed above, examples of medical devices or medical prostheses on which coating material can be deposited include stents, stent-grafts, grafts, vena cava filters, expandable frameworks, catheters, balloons, and portions thereof It is within the scope of the invention for the coating applicator to travel along the coating pathway more than one time. As discussed above, in some embodiments, the coating pathway 54 extends in only one direction about the circumference of the stent and in other embodiments the coating pathway 54 has portions that extend in an opposite direction about the circumference relative to the previous portion.

Also as discussed above, some of the pathways overlap one another and some pathways extend through the same coating point. Only the pathway that bisects the coating point is the pathway along which the coating applicator deposits coating material at that location. When the coating applicator is on a pathway that extends through a portion of the coating point but does not bisect the coating point, the coating applicator does not deposit coating material at that location.

In one embodiment, the band algorithm does not have an angular limitation so that all coating points within a band are assigned to the same pathway. Thus, each band has only one pathway. The steps of this algorithm includes dividing the stent into bands; assigning the coating points in each band to a single pathway; forming a coating pathway from the pathways; and calculating the coating time of the coating pathway. This process is repeated with different band widths until the lowest calculated coating time is determined Then the stent can be coated using the coating pathway having the lowest calculated coating time. With this algorithm, there is greater rotational movement of the stent during coating of the stent. In some embodiments, the bands are parallel to the longitudinal axis. In other embodiments, the bands are non-parallel to the longitudinal axis.

In at least one embodiment, when the coating device or system applies coating material to the medical device, both the coating applicator and the medical device are in motion when coating material is ejected or emitted from the coating applicator. This is also known as on-the-fly coating, which is discussed in U.S. Pat. No. 7,048,962, incorporated by reference in its entirety. In some embodiments, the coating applicator is moving along a first axis and the medical device is rotating about the first axis at the same time. In this embodiment, due to the simultaneous movement of the coating applicator and the medical device, the coating applicator travels a non-linear path that extends from one end of the stent to the other end of the stent, as described above.

In at least one embodiment, the coating applicator deposits coating material onto the medical device according to a predetermined coating pathway. In some embodiments, the coating applicator deposits coating material onto each coating point as the coating applicator travels along the predetermined coating pathway. In other embodiments, the coating applicator deposits coating material onto less than all of the coating points on the predetermined coating pathway as the coating applicator travels along the predetermined coating pathway.

In summary, a method of coating a medical device includes determining coating locations on a surface of a medical device; determining a plurality of pathways extending from one end of the stent to the other end of the medical device; determining a coating pathway by linking the plurality of pathways; and providing the coating pathway to a coating system or device. The method can further include depositing coating material onto the coating locations by an applicator traveling along the coating pathway.

Computer program product is within the scope of the invention. In at least one embodiment, the computer program product comprises computer-readable program code. In some embodiments, the computer readable program code including program code for performing the pattern based algorithm. In this embodiment, the program code includes program code for selecting a coating point at one end of the stent map; program code for assigning coating points to a pathway wherein each coating point that is on a travel path that has a deviation greater than the user selected maximum angle of deviation being omitted; program code for assigning omitted coating points in each band to a pathway; program code for forming a coating pathway from the plurality of pathways; and program code for calculating the coating time.

In other embodiments, the computer program product comprises computer-readable program code includes program code for performing the band based algorithm. In this embodiment, the program code includes program code for dividing the circumference of a stent into longitudinal bands, each longitudinal band having a width; program code for assigning coating points in each band to a pathway with each coating point that has a deviation relative to the pathway that is greater than the maximum angle of deviation being omitted; program code for assigning omitted coating points in each band to a pathway; program code for forming a coating pathway from the plurality of pathways; and program code for calculating the coating time.

The computer readable program code can further comprise program code for determining a plurality of coating points on a surface of a medical device; and program code for instructing a coating applicator to travel along at least one selected coating pathway at least one time.

The stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A method of coating a medical device, the method comprising:

- dividing the medical device into bands, each band having a predetermined width and each band having a coating point;
- assigning the coating point in each band to a pathway;
- determining a coating pathway, the coating pathway including each pathway of each band;
- calculating the coating time of the coating pathway;
- wherein the assigning, determining, and calculating steps are repeated using incremental increases to the predetermined width until a coating pathway having a lowest calculated coating time is determined; and
- coating the surface of the medical device with coating material deposited from an applicator traveling along the coating pathway having the lowest calculated coating time.

2. The method of claim 1, further comprising identifying coating points on a surface of medical device, the coating points being locations on the surface of the medical device at which coating material is to be deposited.

3. The method of claim 1, the medical device having a longitudinal axis, wherein each pathway has an overall variation of ±3° to about ±9° degrees relative to a the longitudinal axis of the medical device.

4. The method of claim 1, the medical device having a longitudinal axis, wherein each pathway has a plurality of travel paths, each travel path extending between two coating points, each travel path having an angle relative to the longitudinal axis of the medical device that is no greater than a predetermined maximum amount of deviation relative to the longitudinal axis of the medical device.

5. The method of claim 4, wherein the predetermined maximum amount of deviation relative to the longitudinal axis of the medical device is at most about ±45°.

6. The method of claim 1, wherein the pathway to which the coating point in a band is assigned is a single pathway and wherein there is no predetermined maximum amount of deviation relative to the longitudinal axis of the medical device for the single pathway.

7. The method of claim 1, wherein each bank is a longitudinal band.

8. The method of claim 1, wherein the coating point is a plurality of coating points, and each bank has a plurality of pathways.

9. The method of claim 1, wherein each band has a single pathway.

10. The method of claim 1, wherein the pathway is substantially longitudinal relative to a longitudinal axis of the medical device.

11. The method of claim 1, wherein during the coating step, both the coating applicator and the medical device are in motion when the coating material is deposited from the coating applicator.

12. The method of claim 1, wherein during the coating step, the coating applicator travels a non-linear path.

13. The method of claim 1, wherein during the coating step, the coating applicator moves along a first axis and the medical device rotates about the first axis.

14. The method of claim 1, wherein the step of assigning the coating point in each band to the pathway includes omitting any coating point that requires a deviation greater than a maximum angle of deviation from the pathway.

15. The method of claim 14, further wherein any omitted coating point is assigned to an additional pathway.

* * * * *